(12) United States Patent
Klostermeyer

(10) Patent No.: US 6,217,611 B1
(45) Date of Patent: Apr. 17, 2001

(54) MODULAR HEART VALVE PROTHESIS

(75) Inventor: Tammi E. Klostermeyer, Austin, TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/320,023

(22) Filed: May 26, 1999

(51) Int. Cl.[7] .................................................. A61F 2/24
(52) U.S. Cl. ............................................................ 623/2.38
(58) Field of Search ................................ 623/2.1, 2.17, 623/2.2–2.34, 2.37, 2.38, 2.39, 2.41

(56) References Cited

U.S. PATENT DOCUMENTS

| 4,680,031 | 7/1987 | Alonso | 623/2 |
|---|---|---|---|
| 4,995,881 * | 2/1991 | Knoch et al. | 623/2.29 |
| 5,071,431 * | 12/1991 | Sauter et al. | 623/2.4 |
| 5,123,919 * | 6/1992 | Sauter et al. | 623/2.4 |
| 5,314,491 * | 5/1994 | Thongpreda et al. | 623/22.29 |
| 5,383,938 * | 1/1995 | Rohr et al. | 623/22.29 |
| 5,607,465 | 3/1997 | Camilli | 623/1 |
| 5,716,370 | 2/1998 | Williamson, IV et al. | 606/153 |

* cited by examiner

Primary Examiner—David J. Isabella
(74) Attorney, Agent, or Firm—Philip S. Lyren; Timothy L. Scott

(57) ABSTRACT

A heart valve prosthesis including a valve body having a first retainer integrally formed with an outer surface thereof. A grafting assembly is formed to include a stiffening member having an axial bore extending therethrough and a second retainer integral with a surface of the stiffening member. The valve body is mounted within the bore of the stiffening member. A retaining member engages the first and second retainers to limit axial displacement of the stiffening member relative to the valve assembly.

20 Claims, 4 Drawing Sheets

MODULAR HEART VALVE PROTHESIS

BACKGROUND

The disclosures herein relate generally to heart valves and more particularly to modular heart valves.

Heart valves generally include a grafting member such as a sewing cuff, a stiffening ring and a valve assembly. The valve assembly typically includes a valve body and one or more leaflets that are pivotally attached to the valve body. Unitary heart valves are inherently installed as a unitary device requiring mechanical attachment to the associated anatomy of the heart. The implantation of modular heart valves generally entails attaching the grafting member and then attaching the valve assembly.

A limitation of unitary heart valves is that the surgeon cannot readily view beyond this type of heart valve to check for any possible blockages or other anomalies. To view beyond the heart valve, the internal components of the valve assembly must be manually manipulated. The manipulation of the internal components generally entails placing a sharp instrument through the valve assembly. This presents a risk of damaging the internal components of the valve assembly.

Another limitation of integrated heart valves is the technique of securing the graft assembly to the annulus using sutures. This technique is time-consuming and occurs while the patient is on cardiac-by-pass. It is undesirable to keep a patient on cardiac-by-pass for an extended period of time.

Present modular heart valves suffer from one or more limitations. In some instances, present modular heart valves are expensive to manufacture due to costly process steps of forming complex shapes such as helical screw-type threads. Another common limitation is the difficulty in attaching the valve assembly to the grafting member. The space required for implanting these type of prosthetic devices is limited. With this being the case, complex attachment schemes are quite undesirable. U.S. Pat. No. 4,680,031 discloses a "tissue valve type" heart valve prosthesis which has a biocompatible plastic sewing ring adapted to be surgically implanted into the mitral, aortic or tricuspid annulus of the human heart. The sewing ring has internal square threads and a bio-compatible fabric mesh or cloth that is embedded into the sewing ring so that the cloth can be fully wrapped around the sewing ring covering all of its plastic surfaces except for the internally protruding threads. A bio-compatible plastic stent support ring has externally disposed threads to lock with the threads of the sewing ring in approximately one turn, or less. The stent support ring also embeds a bio-compatible fabric mesh which can be wrapped around the stent support ring to cover all of its plastic surfaces, except for the protruding threads, and to form a cloth pocket wherein a solid stent is mounted.

U.S. Pat. No. 5,607,465 discloses a valve for use in a blood vessel, internal to the blood vessel itself. The valve has a bent flexible wire mesh with elasticity and plasticity so as to be collapsible and implantable remotely at a desired site. The wire mesh is bent into three turns, two end ones and a central one, in such a way as to confine a tubular space. The central turn is located at an angle relative to the end turns and mounts a monocusp sail-like valving element. A special catheter is used to collapse the flexible wire mesh to implant it remotely at the desired site and to restore the wire mesh to its original three-dimensional configuration.

U.S. Pat. No. 5,716,370 discloses a technique for replacing a heart valve using minimally invasive methods to reduce the time associated with replacing the valve. This technique includes a sutureless sewing cuff and a fastener delivery tool that holds the cuff against the patient's tissue while delivering two fasteners. The fasteners are delivered two at a time in opposite directions to attach the cuff to the tissue from the inside out. Drawstrings are operated from outside the patient's body and cinch the sewing cuff to the valve body. The cuff is releasably mounted on the tool. The tool stores a plurality of fasteners thereon. Two rows of staggered fasteners are formed whereby fasteners are located continuously throughout the entire circumference of the cuff.

Although attempts have been made to modular heart valve prosthetic devices, to provide improved accessibility to the anatomy below an installed heart valve and to reduce the time required for implantation, these attempts have provided only limited success. Accordingly, there is a need for a heart valve that overcomes the shortcomings of present heart valve assemblies and implantation techniques.

SUMMARY

One embodiment, accordingly, provides a modular heart valve having a valve assembly that is detachably connected to a graft assembly. To this end, one embodiment provides a heart valve prosthesis including a valve body having a first groove extending at least partially around an outer surface of the valve body. A graft assembly is formed to include a stiffening member having an axial bore extending therethrough. The valve body is mounted in the axial bore of the graft assembly. A retaining member resiliently engages a surface of the stiffening member and the first groove of the valve body for limiting axial displacement of the valve body relative to the stiffening member.

A principle advantage of the embodiments presented herein is that the graft assembly can be attached to the annulus separate from the valve assembly. This allows the view of the lower anatomy of the heart to be unobstructed when the graft assembly is being secured to the annulus.

BRIEF DESCRIPTION OF THE DRAWING FIGURES

DETAILED DESCRIPTION

Figure 1:
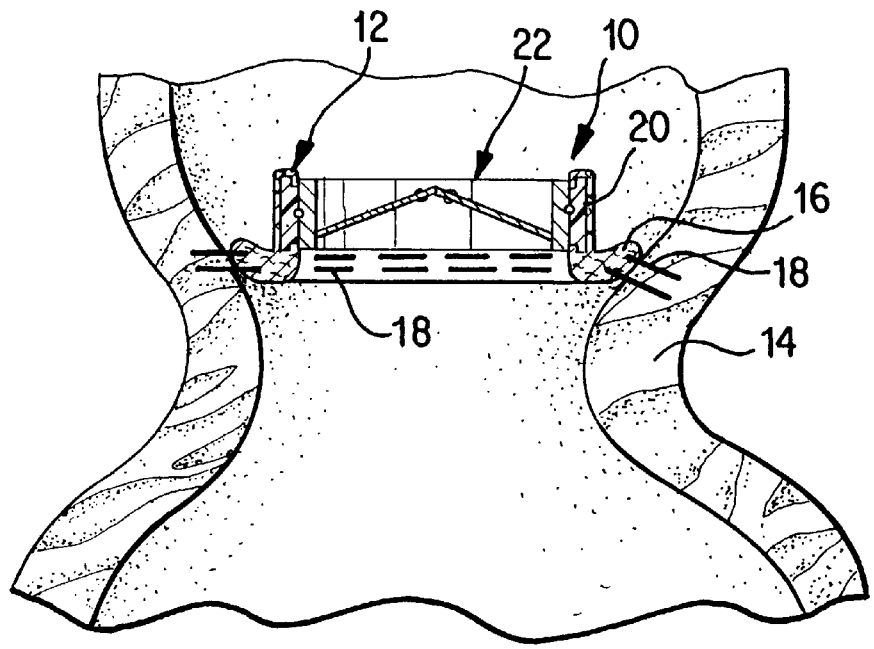
FIG. 1 is a cross sectional view illustrating an embodiment of a heart valve prosthesis implanted in an annulus of a heart.

FIGS. 1 illustrates an embodiment of a heart valve prosthesis 10 implanted in a heart. The heart valve prosthesis 10 includes a graft assembly 12 attached to an annulus 14 of the heart. The graft assembly 12 includes a grafting member 16 attached to the annulus 14 using a plurality of sutures 18, and also includes a stiffening member 20 attached to the grafting member 16. A valve assembly 22 is removably received within the stiffening member 20.

The grafting member 16 may be a fabric sewing cuff made from a commercially-available knitted polyester fabric. The grafting member 16 may be configured to allow for attachment to the annulus 14 using sutures, staples or other suitable means of attachment. The feature of being able to separately install the graft assembly 12 from the valve assembly 22 simplifies the utilization of attachment techniques such as staples that require access to both sides of the annulus.

Figure 2:
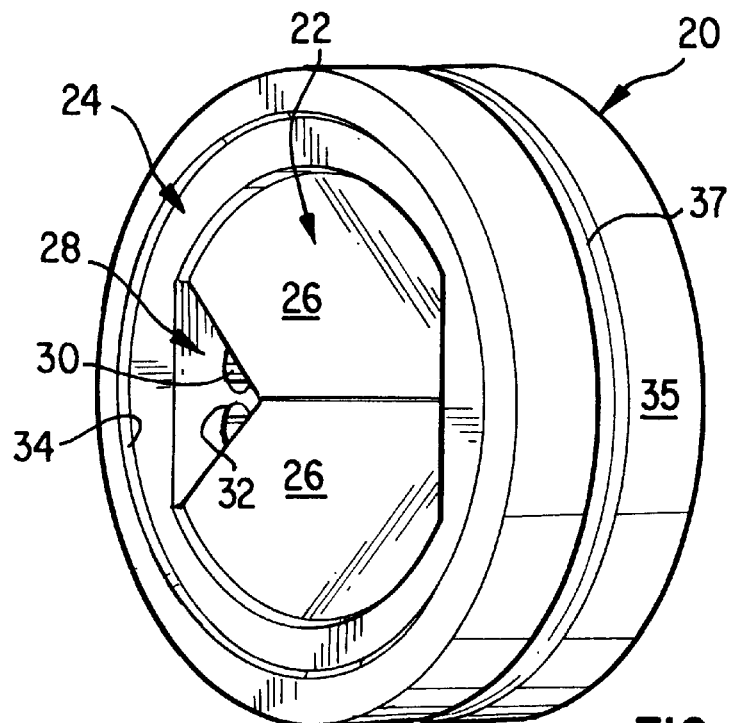
FIG. 2 is a perspective view illustrating an embodiment of a valve assembly mounted in a stiffening member.

FIG. 2 illustrates an embodiment of a valve assembly 22 mounted in a stiffening member 20. The valve assembly 22 includes a valve body 24 and two leaflets 26 pivotally mounted in a central passage 28 of the valve body 24. The leaflets include protruding members 30 captured within apertures 32 formed in an interior surface of the central passage 28. The leaflets 26 may pivot between a closed position C, FIG. 3, during diastolic pressure, and an open position O, FIG. 4, during systolic flow. The valve body 24 may include a tapered edge 33 to aid in inserting the valve body 24 into the stiffening member 20, FIG. 2, during implantation of the heart valve 10.

Figure 3:
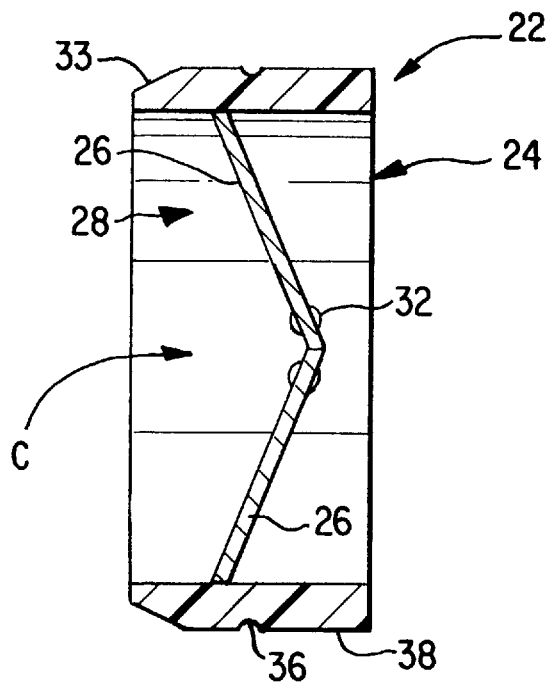
FIG. 3 is a cross-sectional view illustrating an embodiment of a valve assembly with leaflets in the closed position.
Figure 4:
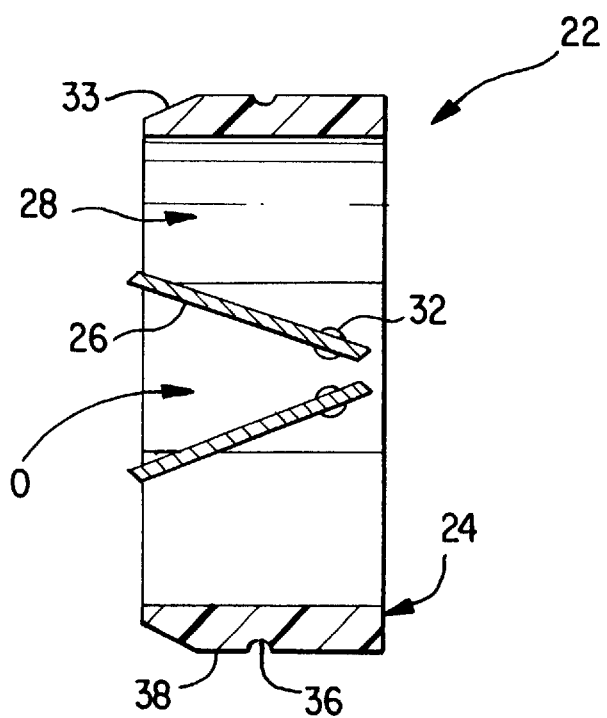
FIG. 4 is a cross-sectional view illustrating an embodiment of a valve assembly with leaflets in the open position.

The valve body 24, FIGS. 3 and 4 is preferably made of a material such as Pyrolite, which is a material manufactured by Sulzer Carbomedics that offers material properties such as improved shear strength and ductility. These properties makes Pyrolite a desirable material for applications such as valve body 24. The leaflets 26 may be made of a multi-layer material such as a graphite clad on opposing sides of a layer of Pyrolite. The stiffening member 20, FIG. 2, may be made of a material such as titanium. It is essential that all of the heart valve prosthesis components be made of biocompatible materials.

Figure 6:
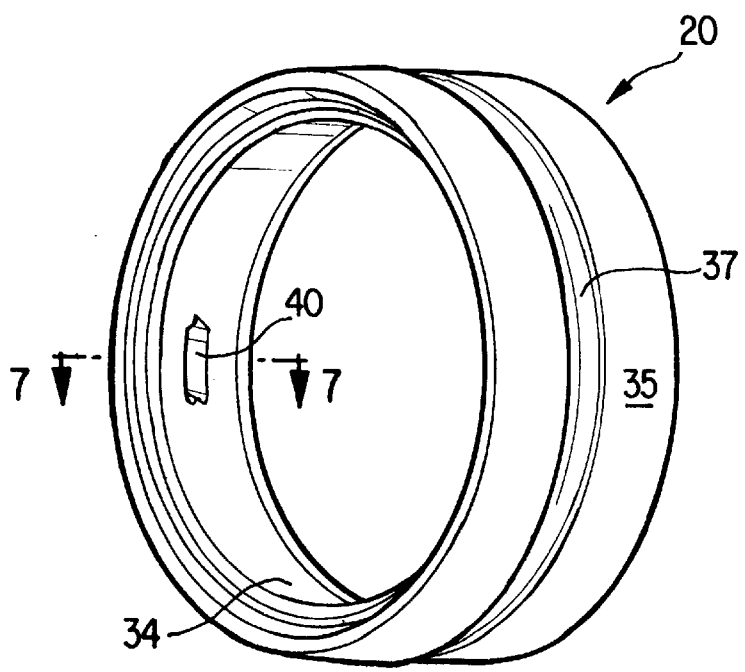
FIG. 6 is a perspective view illustrating an embodiment of a stiffening member.

Referring to FIGS. 2 and 6, the stiffening member 20 includes a bore 34 in which the valve assembly 22 is received. The valve body 24, FIGS. 3 and 4, includes a groove 36 formed in an outer surface 38 of the valve body 24. The stiffening member 20, FIGS. 2 and 6, includes a groove 37 formed in a surface 35 of the stiffening member 20. The outer surface 38 of the valve body 24 is immediately adjacent the bore 34 when valve assembly 22 is mounted within stiffening member 20. One or more windows 40, FIG. 6, are formed in the stiffening member 20 adjacent the groove 37, extending between the outer surface 35 and the bore 34.

Figure 5:
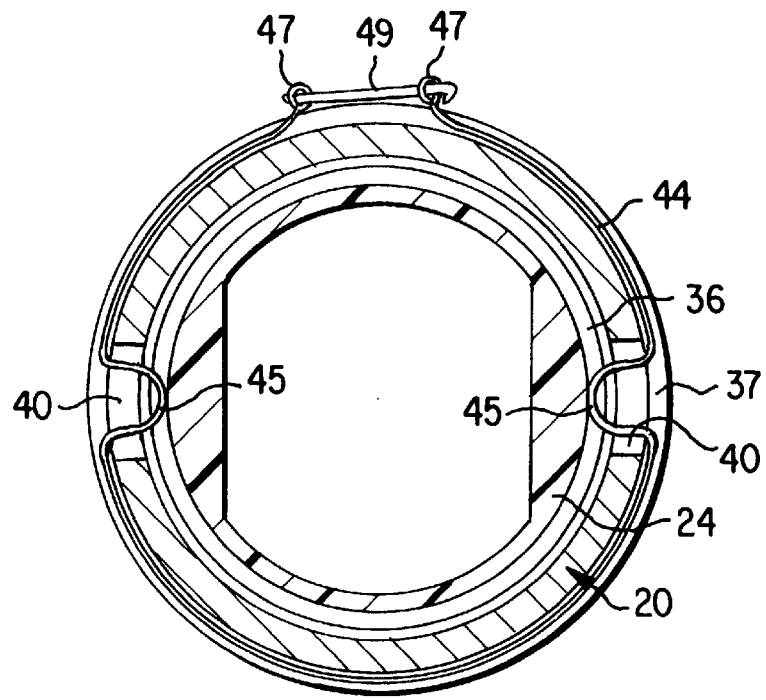
FIG. 5 is an expanded cross-sectional view illustrating an embodiment of a valve body mounted in a stiffening ring.

As best illustrated in FIG. 5, a retaining member 44 is positioned within the groove 37 of the stiffening member 20. The retaining member 44 includes one or more retention portions 45 that extend through windows 40 and engage the groove 36 in the valve body 24. The engagement of the retention portions 45 with the groove 36 limits axial displacement of the valve body 24 relative to the stiffening member 20.

The retaining member 44 is resiliently deformable such that the retaining member 44 is expandable to allow for the valve assembly 22 to be inserted into the stiffening member 20. The retention member 44 may be expanded using a suitable tool or expanded by a feature of the valve body 24 such as the tapered edge 33 illustrated in FIGS. 3 and 4. For an added degree of security, the retention member 44, FIG. 5, may include a locking device such as eyelets 47 formed at the ends of the stiffening member 20. A fastener such as a clip 49 may be attached through the eyelets to secure the retention member 44 in the engaged position. Other types of locking devices such as a mechanical clasp are contemplated.

Figure 7:
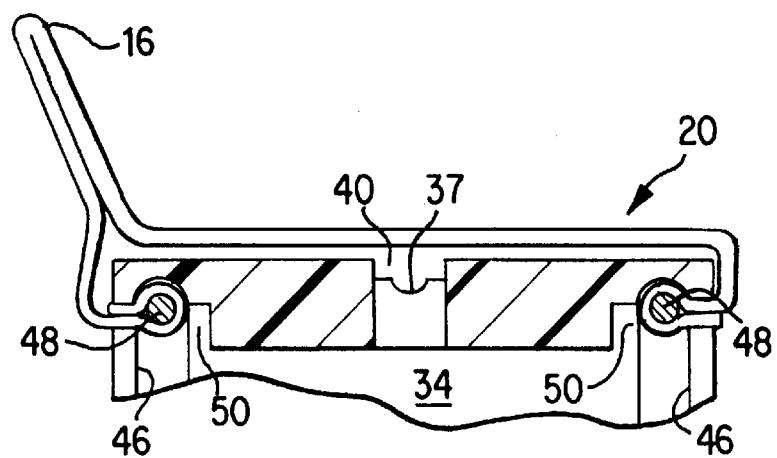
FIG. 7 is a cross-sectional view taken at line 7—7 in FIG. 6.

As best illustrated in FIG. 7, the stiffening member 20 also includes a groove 46 adjacent the edges of the stiffening member 20. Each groove 46 is configured for receiving a retainer 48 such as a snap ring to attach the grafting member 16. A recess 50 is provided adjacent each groove 46. The recess 50 is desirable to limit interference between the grafting member 16 and the valve body 24 when valve body 24 is inserted into the stiffening member 20, FIG. 2. This allows for the valve body 24 to be inserted into the bore 34 of the stiffening member 20 without the valve body 24 binding and being deformed.

Figure 8:
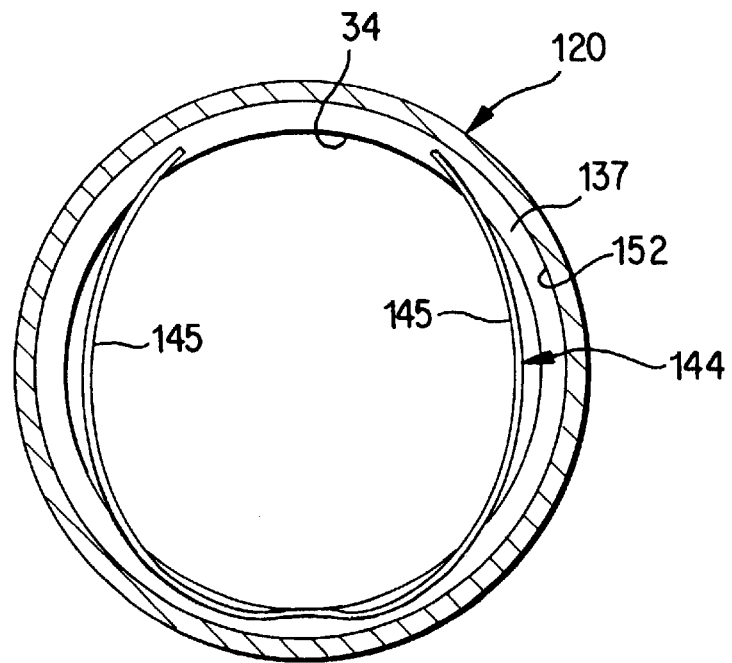
FIG. 8 is a perspective view illustrating an alternate embodiment of a stiffening member and retaining member.

FIG. 8 illustrates an embodiment of a stiffening member 120 in which a groove 137 is formed in an interior surface 152 of the stiffening member 120. A preformed retaining member 144 is mounted in the groove 137. The retaining member 144 includes one or more retention portions 145. The groove of a valve body such as the groove 36 in the valve body 24 illustrated in FIGS. 3 and 4 is engaged by the one or more retention portions 145 similar to retention portion 45 illustrated in FIG. 5.

In operation, the stiffening member is attached to the grafting member to form a graft assembly. The grafting member, including the stiffening member, is secured to the annulus using sutures, staples, or other suitable fastening techniques. Following the attachment of the grafting member to the annulus, the position of the graft assembly and the anatomy below the graft assembly may be examined. A valve body is then inserted into the stiffening member using a suitable tool or technique. A retention member mounted in a groove in the stiffening member is expanded to permit the valve assembly to be received in the bore of the stiffening member. When the groove in the stiffening member comes into alignment with the groove in the valve body, the retention member engages the groove in the valve body to limit axial displacement of the stiffening member relative to the valve assembly.

One embodiment provides a heart valve prosthesis including a valve body having a first groove extending at least partially around an outer surface of the valve body. A graft assembly is formed to include a stiffening member having an axial bore extending therethrough. The valve body is mounted in the axial bore of the stiffening member. A retaining member resiliently engages a surface of the stiffening member and the first groove of the valve body for limiting axial displacement of the valve body relative to the stiffening member.

Another embodiment provides a heart valve prosthesis including a valve body having a first retaining means integrally formed with an outer surface thereof. A grafting assembly is provided that includes a stiffening member having an axial bore extending therethrough and a second retaining means integral with a surface of the stiffening member. The valve body is mounted within the bore of the stiffening member. A retainer engages the first and second retaining means to limit axial displacement of the stiffening member relative to the valve assembly.

A further embodiment provides a method of making a heart valve including the steps of forming a valve body having a first groove extending at least partially around an outer surface of the valve body. A graft assembly is formed including a stiffening member having an axial bore extending therethrough for receiving the valve body and also including a second groove in a surface thereof. A retaining member is engaged with the first groove and the second groove to limit axial displacement of the valve body relative to the stiffening member.

As it can be seen, the embodiments presented herein provide several advantages. The graft assembly can be attached to the annulus separate from the valve assembly. The space required for attachment of the valve assembly to the graft assembly is reduced. The view of the lower anatomy of the heart is unobstructed when the graft assembly is being secured to the annulus. The graft assembly can be secured to the annulus using various methods such as sutures, staples or other techniques with reduced potential of damage to the valve assembly or the delicate tissue of the annulus. The position of the cuff can be verified prior to installation of the valve assembly. A defective valve assembly can be replaced without requiring replacement of a non-defective graft assembly.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A modular heart valve prosthesis, comprising:
   an independently implantable graft assembly module including
      a stiffening member having an axial bore extending therethrough, and having an inner surface and an outer surface a grafting member secured to said stiffening member at the outer surface thereof, and
      a retaining member resiliently engaging said outer surface of the stiffening member, at least a first part of said retaining member extending through said stiffening member and
   a valve module insertable in said graft assembly module after implantation of said graft assembly module, said valve module including a valve body having a first groove extending at least partially around an outer surface of the valve body, said valve module being selectively secured in said graft assembly module by said first part of said retaining member engaging said first groove.

2. The heart valve prosthesis of claim 1 wherein the retention member engages the first groove of the valve body in response to the valve body being inserted into the bore of the stiffening member.

3. The heart valve prosthesis of claim 1 wherein a second groove is formed in said outer surface of the stiffening member, the retaining member engaging the second groove.

4. The heart valve prosthesis of claim 1 further comprising at least one window formed in the stiffening member, each window extending between said outer surface and the bore of the stiffening member, a portion of the retention member extending through the window.

5. The heart valve prosthesis of claim 4 wherein the retaining member is an elongated resilient clip having first and second retention portions, the first and second portions extending through a respective window in the stiffening member.

6. The heart valve prosthesis of claim 1 wherein the valve body includes a tapered portion adjacent an edge of said outer surface of the valve body.

7. The heart valve prosthesis of claim 1 wherein the retaining member is a resiliently deformable clip.

8. The heart valve prosthesis of claim 1 wherein the grafting member is a fabric sewing cuff.

9. The heart valve prosthesis of claim 1 further comprising a plurality of leaflets pivotally mounting to an inside surface of the valve body.

10. The heart valve prosthesis of claim 1 wherein the stiffening member has an annular cross section.

11. The heart valve prosthesis of claim 1 said retaining member has two ends, both ends extending through said stiffening member and said retaining member further comprising means for fixedly securing said two ends of the retention member in a selected position relative to said two ends.

12. The heart valve prosthesis of claim 11 wherein the means for securing is a clip.

13. A method of implanting a heart valve, comprising the steps of:
   forming a valve body having a first groove extending at least partially around an outer surface of the valve body;
   forming a graft assembly including a stiffening member having an axial bore extending therethrough for receiving the valve body and also including a second groove in a surface thereof; a grafting member secured to an outer surface of said stiffening member, and a retaining member in the second groove of the stiffening member,
   implanting said graft assembly in the cardiovascular system of a patient,
   inserting said valve body into said axial bore of said stiffening member of the implanted graft assembly, until said retaining member engages the first groove of the valve body to limit axial displacement of the valve body relative to the stiffening member.

14. The method of claim 13 wherein the step of forming a graft assembly includes the step of forming at least one window in the stiffening member extending between the outer surface and the bore of the stiffening member and wherein said second groove is on said outer surface of said stiffening member and only a portion of said retaining member extends through said windows in said stiffening ring.

15. The method of claim 13 wherein the step of forming a valve body includes the step of forming a tapered portion adjacent an edge of said outer surface of the valve body and wherein said step of inserting said valve body into said stiffening ring includes forcing said retaining means outwardly with said tapered portion.

16. The method of claim 14 wherein said stiffening member has at least two windows and a portion of the retaining member extends through each of said windows and wherein the step of engaging the resilient member to limit axial displacement includes the step of engaging first and second retention portions of the retention member in the first groove of the valve body.

17. The method of claim 13 wherein said retaining member comprises a first and a second end, said ends extending through said grafting member and wherein said step of inserting said valve body further includes securing said ends in a selected position relative to each other.

18. The method of claim 17 wherein said step of securing said ends includes clipping said ends together.

19. The heart valve prosthesis of claim 5 wherein said clip comprises a wire contoured to lie generally along said outer surface of said stiffening member and wherein said first and second portions comprise radially inwardly extending arcs.

20. The heart valve prosthesis of claim 1 wherein at least an end of said retaining member extends through said stiffening member.

* * * * *